US009833197B1

(12) United States Patent
Elhawary et al.

(10) Patent No.: US 9,833,197 B1
(45) Date of Patent: Dec. 5, 2017

(54) SYSTEM AND METHOD FOR MONITORING SAFETY AND PRODUCTIVITY OF PHYSICAL TASKS

(71) Applicant: One Million Metrics Corp., New York, NY (US)

(72) Inventors: Haytham Elhawary, White Plains, NY (US); Aditya Bansal, New York, NY (US); Firdaus Janoos, Jersey City, NJ (US); Selim Youssry, New York, NY (US)

(73) Assignee: One Million Metrics Corp., New York, NY (US)

( * ) Notice: Subject to any disclaimer, the term of this patent is extended or adjusted under 35 U.S.C. 154(b) by 290 days.

(21) Appl. No.: 14/660,578

(22) Filed: Mar. 17, 2015

Related U.S. Application Data

(60) Provisional application No. 61/953,934, filed on Mar. 17, 2014, provisional application No. 62/110,630, filed on Feb. 2, 2015.

(51) Int. Cl.
A61B 5/00 (2006.01)
A61B 5/11 (2006.01)

(52) U.S. Cl.
CPC .......... *A61B 5/7275* (2013.01); *A61B 5/0022* (2013.01); *A61B 5/1116* (2013.01); *A61B 5/1121* (2013.01); *A61B 5/6823* (2013.01); *A61B 5/6824* (2013.01)

(58) Field of Classification Search
CPC ....... A61B 5/7271; A61B 5/7275; A61B 5/11; A61B 5/1118; A61B 5/1124; A61B 5/0024; A61B 5/746; A61B 5/747; A61B 5/1116; A61B 5/1121; A61B 5/6823; A61B 5/6824; A61B 5/0022; G06Q 40/08; G06Q 50/22; G08B 21/02
See application file for complete search history.

(56) References Cited

U.S. PATENT DOCUMENTS

| | | | |
|---|---|---|---|
| 7,457,678 B2 | 11/2008 | Smith et al. | |
| 7,698,830 B2 | 4/2010 | Townsend et al. | |
| 7,797,771 B1 | 9/2010 | Bossen et al. | |
| 8,149,126 B2 | 4/2012 | Little et al. | |
| 8,206,325 B1 * | 6/2012 | Najafi | A61B 5/1116 600/587 |
| 8,638,228 B2 | 1/2014 | Amigo et al. | |
| 8,712,827 B2 | 4/2014 | Mollicone et al. | |
| 8,942,662 B2 | 1/2015 | Pan et al. | |
| 9,504,390 B2 * | 11/2016 | Osorio | A61B 5/0205 |
| 9,532,761 B2 * | 1/2017 | Luo | A61B 6/505 |
| 9,569,798 B2 * | 2/2017 | Biemer | G06Q 40/08 |

(Continued)

OTHER PUBLICATIONS

International Search Report, dated May 26, 2016, with Written Opinion for International Application No. PCT/US2016/016062.

*Primary Examiner* — Max Hindenburg
(74) *Attorney, Agent, or Firm* — Myers Wolin, LLC

(57) ABSTRACT

A method for monitoring workplace safety and evaluating risks during lifting activities is provided, the method comprising receiving signals from wearable first and second devices, identifying portions of the signals corresponding to lifting activities, excerpting the portions of the signals corresponding to lifting activities, and calculating risk metrics based on measurements extracted from the excerpted portions of the signals, the risk metric indicative of high risk lifting activities.

25 Claims, 4 Drawing Sheets

(56) References Cited

U.S. PATENT DOCUMENTS

| | | |
|---|---|---|
| 9,629,559 B2 * | 4/2017 | Maarek ............... A61B 5/0205 |
| 9,633,538 B1 * | 4/2017 | Kozloski ............... G08B 21/02 |
| 2007/0250286 A1 | 10/2007 | Duncan et al. |
| 2009/0135009 A1 | 5/2009 | Little et al. |
| 2011/0183305 A1 | 7/2011 | Orbach |
| 2011/0213278 A1 | 9/2011 | Horak et al. |
| 2012/0083676 A1 | 4/2012 | Wolfberg et al. |
| 2013/0103416 A1 | 4/2013 | Amigo et al. |
| 2013/0331993 A1 | 12/2013 | Detsch et al. |
| 2014/0135592 A1 | 5/2014 | Ohnemus et al. |
| 2014/0163337 A1 | 6/2014 | Horseman |
| 2014/0266737 A1 | 9/2014 | Caldwell |
| 2014/0317135 A1 | 10/2014 | Stivoric et al. |
| 2014/0347265 A1 | 11/2014 | Aimone et al. |

\* cited by examiner

SYSTEM AND METHOD FOR MONITORING SAFETY AND PRODUCTIVITY OF PHYSICAL TASKS

CROSS-REFERENCE TO RELATED APPLICATION

This application claims the benefit of U.S. Provisional Patent Application No. 61/953,934, filed Mar. 17, 2014, and U.S. Provisional Patent Application No. 62/110,630, filed Feb. 2, 2015, the contents of each of which are incorporated by reference herein in its entirety.

FIELD OF THE INVENTION

The system and method relate to monitoring workplace safety and productivity and generating recommendations to improve such safety and productivity.

BACKGROUND

In industries that require physical manipulation of objects or people, such as material handling, patient handling, manufacturing, or construction, workers often perform a variety of manual tasks such as lifting loads, moving loads from one location to another, pushing and pulling carts or trolleys, complex assembly and manipulation of components using specific motions and using vibration and impact tools. Often these motions require an intense physical effort, and therefore the repetition of these tasks over time can cause fatigue and injury.

Wearable technology has been used extensively in the consumer space to quantify, for example, the number of steps taken, distance traveled, length and quality of sleep and other metrics, but wearable technology has not been able to consistently evaluate safety metrics in the materials handling industry.

Many risks associated with material handling workers exist, including repetitive stress injuries based on extended physical effort over prolonged periods of time.

Current solutions are mostly limited to physical inspection by specialists, since there is a lack of effective tools to predict when lifting posture is incorrect, or when fatigue results in a risky or dangerous change of posture or non-ergonomic lifting techniques when performing tasks. Typically, specialists inspect the workplace and observe tasks, or review video footage provided by the employer. In either case, inspection is typically performed over only a limited period of time, usually 5-60 minutes. Without effective tools, employers (and workers themselves) have difficulty predicting and preventing injury.

Further, while workers are taught correct material handling techniques, such techniques are not tailored to the strengths of a particular worker. Different workers can do a particular task in multiple ways because of varying body types and abilities. Better monitoring of task performance incorporating information about the particular worker involved may allow for customized training techniques.

Further, there is a lack of productivity measuring tools for individual workers, as it is rarely possible to measure in real-time the number and quality of tasks a specific worker is performing including their speed and variation over time. This information could allow managers to optimize productivity or to devise novel forms of incentives based on productivity.

Finally, tasks are typically divided among the workers based partially on physical ability. However, the physical ability to do a specific task is determined based on visual observation without any detailed insights on the actual motion of a worker's body. Quantifying body motion can help supervisors factor such information into task and shift assignments. Therefore, additional information related to the aspects of task performance that increase injury risk can inform the design of a workplace, design of shifts, and assignment of tasks.

Existing systems for analyzing the safety and productivity of material handling tasks by analyzing motion have limited real-world applications due to inherent limitations.

Motion detection based platforms, such as optical systems using complex cameras and sensors, are expensive and are of limited use in a warehouse setting as they require line of sight which is not always possible in crowded warehouse or factory environments.

Electromagnetic based motion sensor systems produce errors when they are close to ferromagnetic materials often present in industrial settings, are expensive and typically require cabling from sensors to processing units, making their continued use impractical in a warehouse setting.

Existing devices provide very limited motion information and are typically bulky and impractical. Existing systems cannot extract adequate information to fully implement risk models, and typically require manual input of risk variables that cannot be measured by the device alone.

There is a need for a fully automatable system and method that can monitor physical activity of individual workers and evaluate safety and productivity both for individuals and for a workspace as a whole. There is a further need for a platform that can incorporate such evaluations into recommendations for improving the technique of individual workers and physical characteristics of the workplace environment.

SUMMARY

A computer-based method for identifying risk during lifting activities is provided, wherein a computing device receives a first signal from a wearable first device indicative of physical characteristics of the first device over time and receives a second signal from a wearable second device indicative of physical characteristics of the second device over time. The computing device identifies, from the first signal and/or the second signal, an initiation time for a lifting activity performed by a wearer of the first device and the second device. The computing device then excerpts a first signal segment from the first signal for a time period following the initiation time for the lifting activity, and excerpts a second signal segment from the second signal for a time period following the initiation time for the lifting activity.

The computing device then calculates measurements of the wearer for the time period during the lifting activity from the first signal segment and the second signal segment and calculates a risk metric from a risk model based on the measurements of the wearer for the time period during the lifting activity, the risk metric being indicative of high risk lifting activity.

The computing device may also determine a conclusion time for the lifting activity and may perform the method continuously over the course of an evaluation period in order to evaluate multiple lifting activities. Such a platform may calculate a cumulative risk metric, and may generate feedback to a worker wearing the devices when the cumulative risk metric indicates high risk.

The computing device may also determine a physical location or a lifting activity corresponding to individual lifting activities, such that risk metrics may be correlated with locations or activities. Similarly, the computing device may then provide recommendations related to the particular location or activity corresponding the increased value of the risk metric. For example, such a platform may recommend avoiding lifts beginning near the floor of the warehouse in a specific location within the warehouse.

Measurements extracted from the signals may correspond to a horizontal location of the first device relative to a second device, a vertical location of the first device relative to a floor at the initiation time of the lifting activity, a vertical location of the first device relative to the floor following the lifting activity, a rotation angle of the second device, indicating rotation of the worker's trunk, a frequency of lifting activities during the evaluation period, and a duration of the evaluation period. These values may be used to determine a risk metric in the form of a maximum weight of a package that should not be exceeded, for example.

Additional metrics may be calculated as well, such as productivity metrics, and in some embodiments, the data provided by the devices may be used to, for example, estimate the weight of a package being lifted based on angular velocity of a sensor mounted on a workers wrist.

DETAILED DESCRIPTION OF THE PREFERRED EMBODIMENTS

Figure 1:
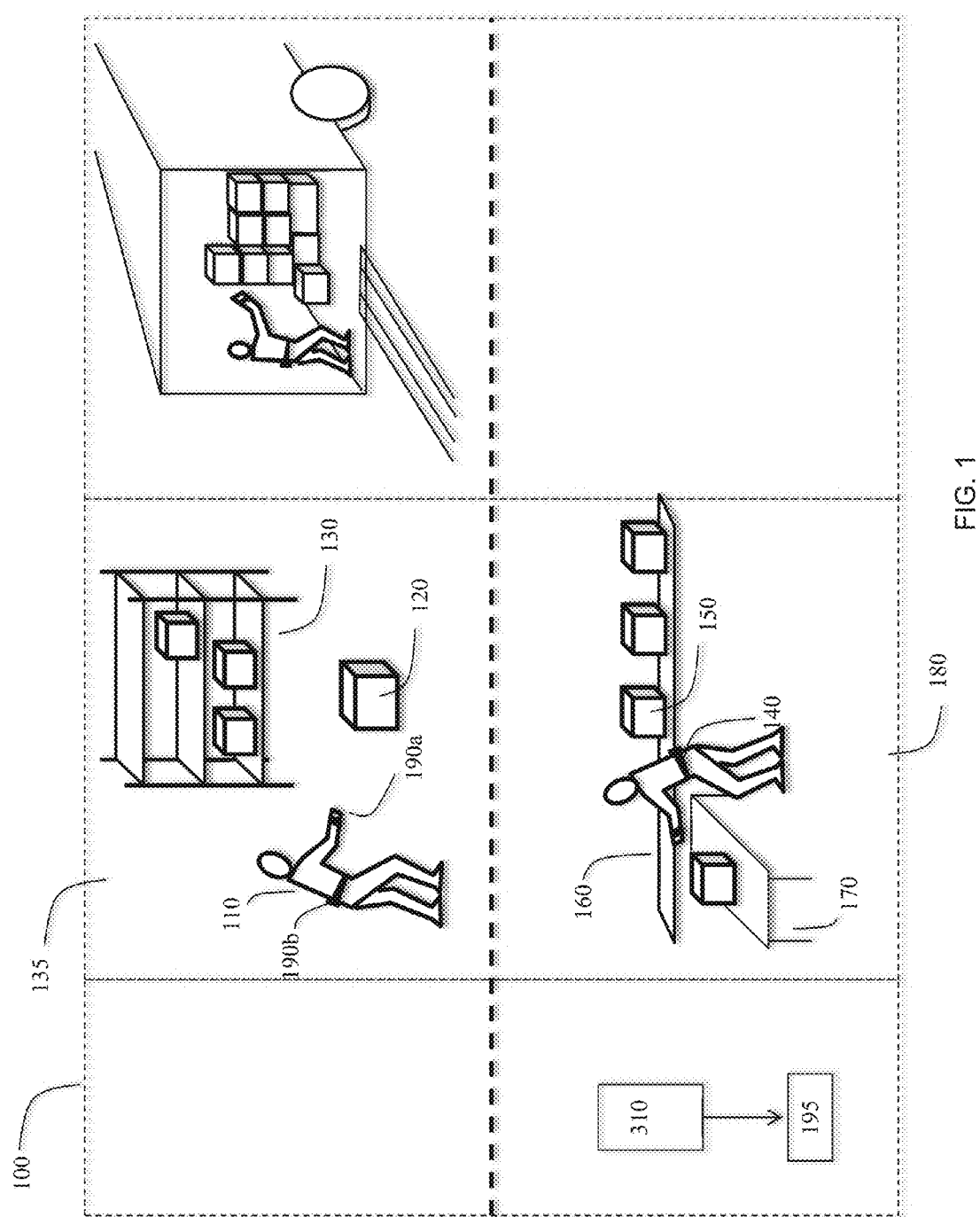
FIG. 1 illustrates a physical environment for implementing a method for monitoring safety.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Figure 2:
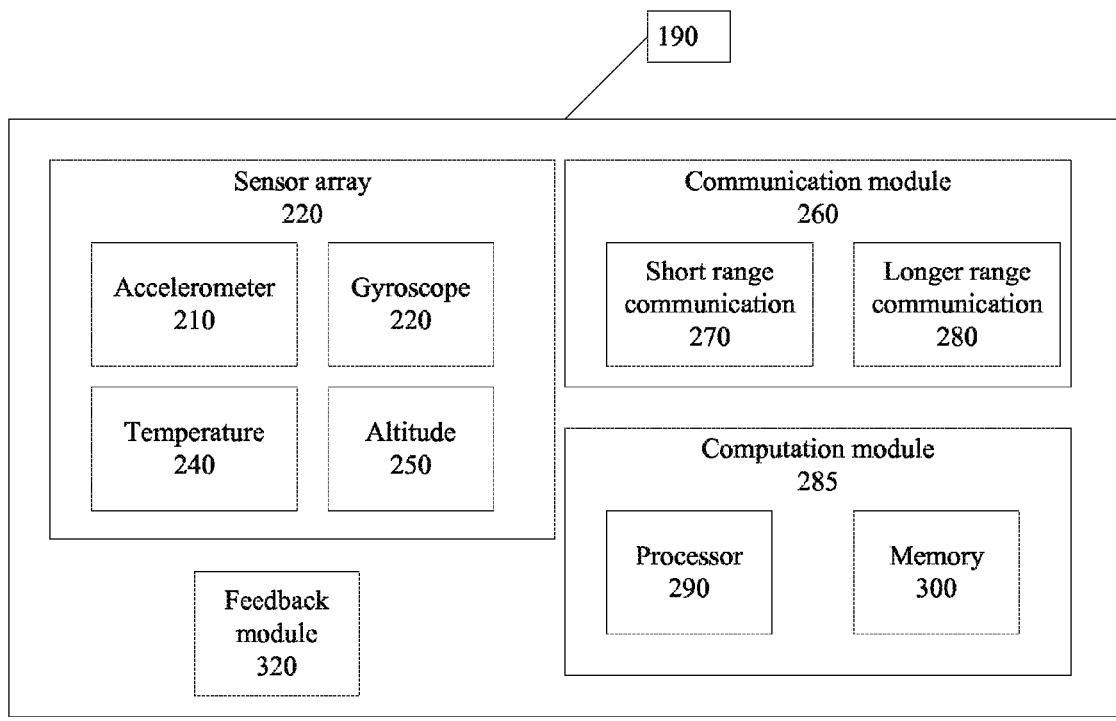
FIG. 2 is a schematic for a sensor for use in implementing the method.
Figure 3:
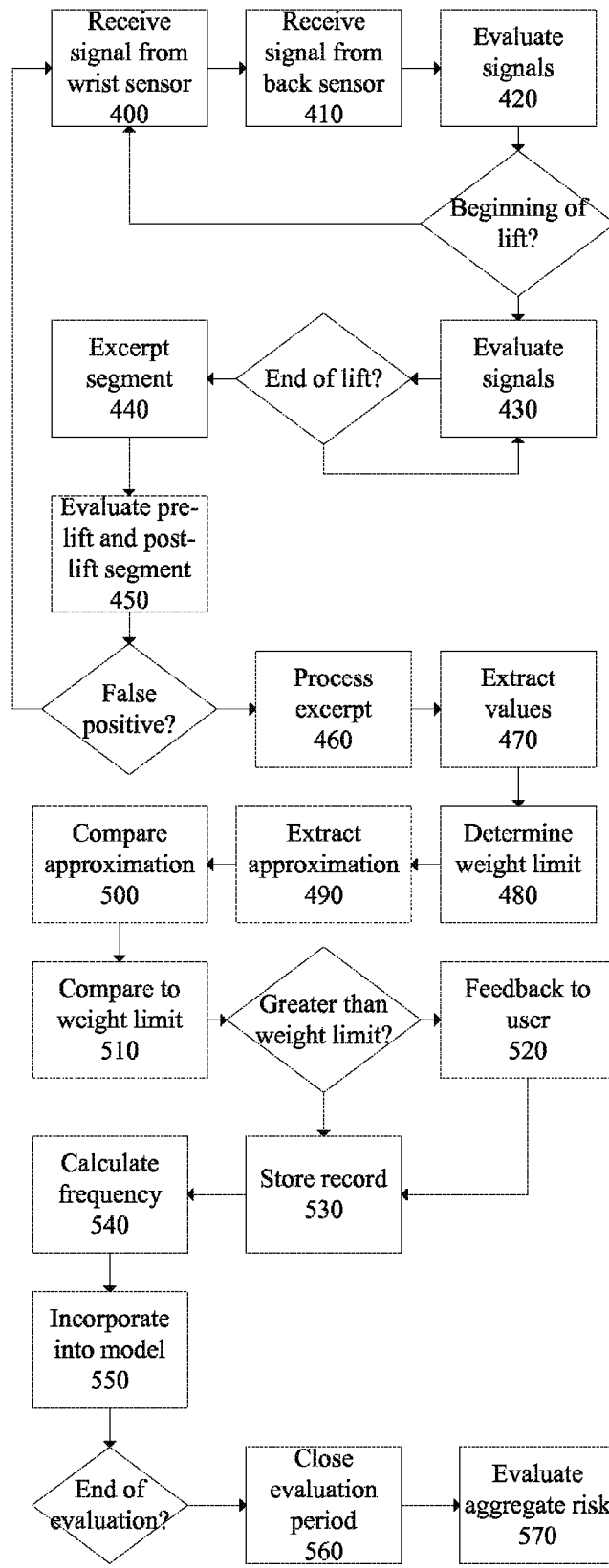
FIG. 3 is a flowchart illustrating such a method.

FIG. 1 illustrates a typical environment in which the system and method monitoring safety and productivity is deployed, FIG. 2 is a schematic for a sensor for use in implementing the method, and FIG. 3 is a flowchart illustrating such a method.

As shown in FIG. 1, workers may be deployed to various locations within a warehouse 100 and may be required to perform a variety of repetitive material handling tasks at each location. For example, a first worker 110 may lift an object 120 from the floor to a shelf 130 in a first sector 135 within a warehouse 100, while a second worker 140 may lift a separate object 150 off of a shelf 160, rotate, and transfer it to a table 170 in a second sector 180 of the warehouse 100.

Each of the first worker 110 and the second worker 140 would typically be wearing at least two sensors 190a, b for recording movement. Typically, the sensors used would be a wrist sensor 190a, ideally located on the wrist or forearm of the dominant hand, and a back sensor 190b, ideally located approximately at the height of the L1 and L2 vertebrae, but other sensor types may be implemented as well. The wrist sensor may incorporated into a wrist device, such as a bracelet or a wristwatch, and the back device may be incorporated into a chest strap, weight belt or back brace, for example.

A server 310 may further be included in the warehouse 100 for receiving data from the wrist sensor 190a and the back sensor 190b and storing records of activity performed by workers 110, 140. In some embodiments, signals generated and transmitted by the sensors 190 are received and processed by the server 310. In some embodiments, results of the methods discussed below are generated and retained by the sensors 190 and are used to provide immediate feedback to workers 110, 140. In some embodiments, the results are transmitted to additional terminal devices 195 to be accessed by a third party, such as a manager, or by the workers themselves 110, 140. While the warehouse 100 shown includes a physical server, it will be understood that the server may be a cloud server or may be coupled to a cloud server to maintain a platform implementing the method described.

As shown in FIG. 2, each of the sensors 190 may include a sensor array 200 including a 3-axis accelerometer 210, a 3-axis gyroscope 220, a 3-axis magnetometer 230, a temperature sensor 240, and an altitude sensor 250, such as a barometric pressure sensor. Each sensor 190 may further include a communication module 260 which may include a short range communication device 270 for enabling communications between a first sensor 190a and a second sensor 190b worn by a single user, and a longer range communication device 280 for connecting, for example, to a Wi-Fi or cellular network. Each sensor 190 may further include a computation module 285, including a processor 290 and a memory 300.

Accordingly, each of the sensors 190a, b, may communicate with each other using the short range communication device 270 and with the server 310 using the longer range communication device 280. Signals generated by the sensors 190 may be processed at the individual sensors, may be combined and processed on either one of the sensors, or may be transmitted to the server 310 or other centralized platform for analysis. The sensors may further incorporate a feedback module 320 for providing feedback to the user. For example, the feedback module 320 may include a motor for generating vibration and providing haptic feedback, in response to the output of the method. The sensors may further include batteries for providing power to the various modules therein. The sensors may further incorporate LEDs, displays, or other methods for delivering feedback to the workers 110, 140 wearing the sensors.

While the components of the two sensors 190a, b are described identically, in some embodiments, the sensors comprise different components. For example, the wrist sensor 190a may not include a longer range communication device 280 or a computation module 280 and may instead immediately transmit signal data to the back sensor 190b. The back sensor may then process the data and transmit results to the server 310.

Other implementations are possible as well. For example, all signals may be immediately transmitted from the sensors 190a, b, to the server 310 which in turn implements the methods described. For the purposes of outlining the methods performed, the methods will be described with respect to such a platform. However, it will be understood that the calculations may be performed at any one of the devices described, or across a combination of the devices discussed.

Accordingly, while workers perform material handling tasks, including lifting objects 120, the server receives both a signal from the wrist sensor 190a indicative of the movement of that sensor over time (400) and a signal from the back sensor 190b indicative of the movement of that sensor over time (410). This may be received in the form of a data stream or a transient signal, or it may be received in the form of chunks of data received consecutively.

The server then evaluates (420) both signals to determine if any portion of the signal represents the initiation of a lifting activity. If a lifting activity is identified in the data, the server then further evaluates (430) both signals to identify an end point of the lifting activity. In some embodiments, this detection of an initiation of a lifting activity and an end point of lifting activity is by way of a rules based approach directly using variables obtained from the sensor data, or based on variables detectable after only minimal signal processing. This rules based approach may include, for example, measuring the back angle with respect to the gravity plane and determining when it passes a threshold. This type of threshold may be static or variable, depending on other elements of the lift. Arm elevation angles may further be used to detect lifts above the shoulder, for example.

In some embodiments, the signals are used to identify only an initiation of a lifting activity, but not an end point of the lifting activity. In such an embodiment, a lifting activity may be assigned a specified time limit, such that the lifting activity is assumed to have concluded after a fixed amount of time has passed.

In embodiments with only minimal signal processing prior to identifying the initiation of a lift may comprise only filtering of data to reduce noise and cancel any drift. Typically, filtering is applied, such as a band pass filter, to ensure that more resource intensive processing is applied only once a lifting activity is detected within the more minimally processed data. For example, drift in height sensor data and gyroscope data may be filtered to reduce noise prior to identifying a lifting activity, and then the filtered data may be utilized to detect the initiation of a lifting task with a reduced number of false positives.

In some embodiments, the lifting activity will be single lifting motion. In others embodiments, the lifting activity may comprise the entirety of the moving of an object from a first location to a second location. For example, the lifting activity may comprise a first user 110 picking an object 120 up off the floor and placing it on a shelf 130. Similarly, the lifting activity may comprise a second user 140 picking up an object 150 off of a shelf, rotating, and placing the object on a table 170. Alternatively, the lifting activity may be a simple lifting action in preparation for a secondary action, such as walking with the package.

One a beginning and end point of a lifting activity is identified, the portion of the signals from the wrist sensor and back sensor between the initiation and end point of the lifting activity are excerpted (440) from the signal to generate a first segment of data corresponding to lift data from the wrist sensor and a second segment of data corresponding to lift data from the back sensor.

In some embodiments, data from the point of time of the initiation of the lifting activity is taken and is processed immediately upon detecting the initiation of a lifting activity. In such a way, risk models depending only upon static posture at the time of lifting may be implemented immediately and may provide results before the completion of the lifting activity.

Optionally, the method may then evaluate (450) a portion of the signals from the time period immediately before lift and immediately following the lift. This may be used, for example, to eliminate false positives prior to incorporating such results into statistics being reported. For example, when a worker bends over to lift something outside the scope of his task, such as a worker bending down to lift a pen from the floor and place it in his pocket. In such an example, the initial back bending angle and lowering of the wrist, as measured by wrist height, would indicate a lifting event. However, since the wrist would then align with hip of the worker and the back of the worker would straighten, this would not be considered a lifting event. Accordingly, the portion of the signal immediately following the lift may then clarify that the lift detected would constitute a false positive for the purpose of statistics being gathered.

Once the portions of the signals corresponding to lifts are excerpted, the method processes (460) the excerpted portions of the signal to extracts metrics required for risk models being evaluated. The processing of the excerpted portions of the signal typically incorporates methods designed to increase signal to noise ratio and otherwise improve the quality of the data. This may include methods such as low pass filtering, Kalman filters, Gaussian moving averages etc., all of which combine to reduce the noise in the signal and remove unwanted drift of signals, such as the barometric pressure signals, from the sensor data. From the signal processing, we compute several new variables such as back sagittal angle or wrist elevation angle, as discussed further below.

In some embodiments, some amount of signal processing occurs prior to step 420 so that a signature in the data corresponding to a lifting activity may be more consistently identified. Such a signature may be used to detect sequences associated with lifting tasks, such as box grabbing, carrying, and dropping. In other embodiments, the data is checked after the excerpts have been processed to confirm that a lifting activity has indeed occurred. For example, the data from the back sensor 190*b* may be monitored to determine when a worker's back has bent over a certain amount. This information may be coupled with data from the wrist sensor 190*a* to increase accuracy. While the method is described with respect to a lifting task, it will be understood that the task may be any number of physical tasks, such as a known sequence of motions for assembling a device or a specific task such as rebar assembly within the construction industry.

Where the risk model being evaluated is the NIOSH lifting equation risk model, the method extracts (470) from the data the following values:

H—a horizontal location of the object being lifted relative to the body. This may be determined, for example, by evaluating the horizontal difference in location between the wrist sensor 190*a* and the back sensor 190*b* and accounting for known offsets based on the angle of the back sensor 190*b*, and the known thickness of the trunk of the worker being evaluated, as well as the offset from the workers wrist to his hands.

V—a vertical height of the object being lifted relative to the floor. This may be determined, for example, using a height sensor in the wrist sensor 190*a*, such as the barometric pressure sensor 250 and further utilizing some of the signal processing techniques discussed below.

D—distance the object is moved vertically. This may be determined by calculating the difference in height at the time of initiation of the lift and the conclusion of the lift. In cases where the lifting process being evaluated includes both picking up and putting down the object, this may be the difference between the highest and lowest heights measured during the process.

A—asymmetry angle is a measure of how much the workers back is twisted during the process. Where a worker 140 picks up a package 150 in a first location 160 and places it down in a second location 170, the amount of rotation of the workers back is measured and evaluated. This may be evaluated by extracting the data from the gyroscopic sensors in the back sensor 190*b* and applying an offset based on the workers trunk thickness.

F—frequency of lifts performed, as computed from lift detection algorithms.

In some embodiments, duration of lifting tasks may be implemented, as computed by the time lifting activities have occurred and have been detected by lifting algorithms.

In some embodiments, an additional variable, C, may be incorporated and evaluated to assess the quality of the grip of a worker on a package.

The processing associated with these variables, as well as those below may include computing a gravity vector from quaternion data, which is obtained from the fusion of gyroscope and accelerometer sensor data. In such embodiments, acceleration in both horizontal plane and vertical direction may then be computed using the gravity vector. Threshold based outliers may then be removed from the data. Components of the back and wrist elevation angles are then computed using components of the gravity vectors.

Several required variables may be detected or confirmed by way of machine learning algorithms. Similarly, the accuracy of lift detection may be improved by way of machine learning algorithms. Such algorithms may further be utilized to confirm the identification of the activity detected, both in terms of improving the detection of true positives and eliminating false positives. More broadly, such algorithms may improve the precision and recall of lift detection and variable evaluation. Statistical features monitored by such machine learning algorithms may include:

Lagged cross—correlations between variables;
Dominant frequency components of the signal;
Movement intensity statistics;
Movement energy statistics;
Signal magnitude area; and
Window duration.

All of these statistics may be monitored over windows of data which may be calculated based on elements of the signal, such as those detected above in steps 420 and 430.

As discussed above, some variables may be detected directly from the sensor data while others require further processing. Since several variables are inferred, rather than detected directly, the method may utilize confidence intervals in the estimates and may report results, as discussed below, in the form of either conservative or aggressive approaches, to calculate risk metrics. Such approaches may be selected by a user operating a platform implementing the methods.

The height of sensors is typically extracted from a barometer, or other types of altimeters. Data from these sensors tend to drift. Accordingly, the drift may be corrected by coupling the sensor data with acceleration data in the gravity direction in a Kalman filter. This may also be done by way of a low pass filter for certain types of altimeters. Further, the height detector may be calibrated by setting the height to a known value upon the initiation of a lift. For example, the height of a back sensor may be set to a fixed value at the beginning of each lift, regardless of whether the worker is, for example, standing on a stool.

In some embodiments, some initial signal processing is applied to the signals upon receipt so that the detection of the beginning of a lifting activity may be made with more accuracy. The initial signal processing may then be followed by more advanced signal processing and machine learning algorithms for extracting remaining variables from the data and for confirming that a lift actually occurred during the time period excerpted from the signal.

Besides travel distance for a specified value between the beginning and conclusion of a lifting activity, each variable may be independently evaluated with respect to the beginning of a lifting activity detected and at a conclusion of a lifting activity detected. For example, where a worker 140 moves a package 150 from a shelf 160 to a table 170, if the worker faces the shelf while doing so and twists his back 90 degrees to deposit the package 150 on the table 170, his angle will be 0 for the beginning of the lifting activity and 90 for the end of the lifting activity.

Other ergonomic risk models may be implemented as well, and may require extracting different values from the data. For example, if implementing the risk model developed by Marras et al using his Lumbar Motion Monitor, the data extracted from the signals may be:

Average twisting velocity of the torso during the lift activity, computed in a way similar to the calculation of the asymmetry angle discussed above, except using angular velocity.

Maximum moment on the lower back, which is computed by multiplying the maximum horizontal distance between the load and the worker's trunk and the weight of the object lifted.

Maximum sagittal flexion of the torso, which is determined by extracting the offset bending angle of the lower back relative to a vertical axis (usually gravity).

Maximum lateral velocity of the torso, which may be determined from the accelerometer gyroscope in the back sensor.

Frequency of lifts specified in lifts per minute, which can be obtained from the frequency of lift detection.

In some embodiments, the risk models specified may be used to calculate a maximum recommended lifting weight based on a workers lifting technique. This is done by using the variables extracted from the signals in a risk model. For example, the NIOSH risk model may be used to calculate a recommended weight limit. Further, the model may be used to calculate a lifting index identifying a risk associated with any particular lifting action or task. Either model may provide numerical results, or those results may be classified in terms of low, medium, and high risk lifts. Similarly, underlying values for variables may be implemented directly in the models, or they may be mapped on to low medium or high values.

Using the NIOSH risk model as an example, a recommended weight limit for a single lift may be calculated by simply determining each of the values discussed above, determining an appropriate multiplier used in the model (typically determined from a table associated with the model, or by calculating an appropriate ratio) and multiplying the relevant multipliers. Accordingly, the recommended weight limit may be determined from the equation RWL=LC*HM*VM*DM*AM*FM where LC is a constant multiplier for the formula, typically 51 lbs., and HM, VM, DM, AM, and FM are the multipliers associated with the calculated values of H, V, D, A, and F respectively. In some embodiments, an additional multiplier may be used to incorporate the duration of lifting tasks. While the NIOSH risk model is described, other risk models may be implemented as well. Further, by dividing an actual weight lifted by the recommended weight limit generated by the NIOSH model, a lifting index may be generated providing an evaluation of the risk associated with a specified lifting activity.

While NIOSH and Marras models are described, other risk models may be utilized as well, such as Liberty Mutual® tables, RUBA, RULA, and others.

In this way, the selected risk model is used (480) to determine a maximum recommended weight for any given lift. Where the risk model used supports a determination for a single point in time, the risk model may be implemented immediately following the detection of an initiation of a lifting activity at step 420. In such an embodiment, the information from the moment of time detected is immediately extracted and processed.

Optionally, the method may extract (490) from the data an approximation of the actual weight of a package lifted. Such an approximation may be calculated by evaluating the angular velocity or acceleration of the wrist sensor 190*a*. In some embodiments, this may be compared (500) to the same metric for a known weight such that the weight of an object may be inferred by comparing the angular velocity of a specified lift by a worker to an angular velocity associated with a lift for a known weight by the same worker. The accuracy of this measurement may be further improved by evaluating data related to the angle of the back sensor 190*b* and similarly mapping it to known angles for known weights by the same worker.

Similarly, metrics correlated with energy applied during a lift may be implemented. Such metrics may draw signals from both the back and wrist sensors and may be used to evaluate the weight of an object lifted.

The various signals evaluated upon identifying a lifting motion may then be used to detect acceleration in the vertical direction in the world frame of reference. Accordingly, when a worker begins a lifting process, the wrist based accelerometer may immediately detect a jerking motion as the height sensor begins to rise from its lowest position. The velocity of the rising motion may then be used as a proxy for effort applied in lifting, which in turn may be used as a proxy for determining the weight of an object lifted. Such an approach may determine both the weight of the object being lifted or, if the weight of the object is known, the fatigue of the worker lifting the object. Either approach will allow the system to determine an effective weight of the object from the perspective of the worker. Including the fatigue of the worker lifting the object in this way may further incorporate a fatigue component in evaluating risk to the worker.

In such an embodiment, the approximate weight or effective weight calculated is then compared (510) to the maximum recommended weight determined at step 480 based on the model.

If the weight lifted is greater than the maximum recommended weight, the sensor may provide feedback (520) to alert the worker to the weight limit. Such feedback may be, for example, haptic or audible feedback. In some embodiments, a combination of feedback methods may be implemented, and the feedback may then be displayed on a screen associated with the device or through an LED, and haptic feedback may be implemented to prompt the user to view the screen.

While the method evaluates individual lifting activities, the server will continue to receive data from the sensors 190*a, b*. Accordingly, the server may then store (530) a record of the first lift in a memory associated with the server and return to step 400 and continue monitoring the sensor data to determine if the worker is performing additional lifting activities. The server typically continues to monitor the data for additional lifting motions over the course of an evaluation period. In some embodiments, once multiple lifts have occurred, the method calculates (540) a frequency associated with the lifting motions identified and incorporates (550) that value into the risk models in order to monitor and evaluate risks associated with repetitive lifts. Such frequency data may be used in the NIOSH model described above, for example, to reduce the maximum recommended weight for a repeated lifting activity based on repetitive stresses and associated risks.

After the conclusion (560) of an evaluation period during which lifting motions are evaluated, the risk models may be used to evaluate (570) aggregate risk over the time period. In some embodiments a worker's shift may be divided into blocks of time, such as half hour blocks, for use as evaluation periods. In some embodiments, the evaluation period is instead the entirety of the worker's shift.

Figure 4:
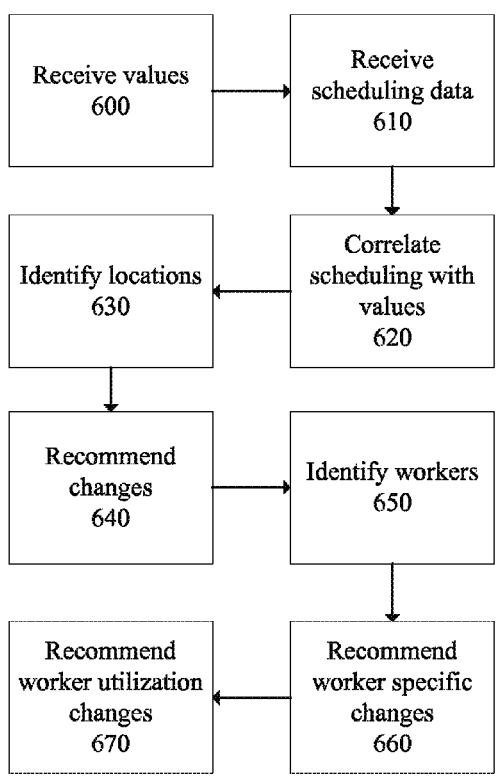
FIG. 4 illustrates a method for generating recommendations.

FIG. 4 illustrates a method for generating recommendations based on the data and risk model outputs received in the method of FIG. 3. The server first receives (600) values for the risk metric calculated in such a method with respect to individual lifting activities for multiple workers.

The server further receives (610) scheduling data for individual workers including information related to the location within a warehouse that each worker is assigned to. This scheduling data typically contains, for each worker, a location at which they would be working at any given time. The server then correlates (620) the scheduling data with the risk metric for individual lifts in order to determine a location for the individual lifting activities associated with the risk metrics calculated.

The server then identifies (630) specific physical locations, in the form of warehouse sector numbers, for example, at which the risk metric illustrates a high risk across multiple workers. The method may then recommend (640) location based changes based on the data underlying the risk metric showing high risk. For example, where the risk metric shows that multiple employees are at increased risk because an object must be lifted from a high location, the platform may recommend lowering a shelf on which objects rest or adding a stool for workers to stand on while lifting. Similarly, if workers consistently rotate their backs excessively while performing a task at a specific location in a warehouse, the platform may recommend adding a conveyor to that sector of the warehouse.

Similarly, the server may identify specific tasks rather than physical locations, that result in increased risks for workers. For example, if the first worker 110 and the second worker 140 both generate increased values of the risk metric when their schedules indicate that they were each performing a specific task. Accordingly, if multiple workers consistently demonstrate increased risk when, for example, unloading trailers, that task may be highlighted as a high risk task, and the platform may recommend a change in the methodology for performing that particular task.

A platform incorporating the method may present this data in a number of ways. For example, it may provide a heatmap illustrating metric values.

Rather than incorporating worker schedules, in some embodiments, the sensors 190 may have an additional module for determining worker location by, for example, incorporating a GPS unit or other geolocation components and processes. Alternatively, the sensors may triangulate the location of workers based on proximity to known landmarks, such as beacons.

Further, data from individual workers may be correlated with personal information for that worker. For example, a specific worker's data may be correlated with that workers height, history of back injuries or other medical issues, or other physical or personal characteristics that may affect performance. Further, measures of physical characteristics may be estimated, such as arm length for workers, which can in turn be used to improve both the ability to infer variable values from signal data and the ability to use the variable values detected.

The server may further identify (650) specific workers with higher average risk metrics than others in specific areas. In such a scenario, the method may recommend (660) changes specific to that worker, such as corrections to the worker's posture, or it may recommend (670) utilizing that worker in a different location in the warehouse where they would not be placed at risk. For example, where a specific worker is shorter than others and therefore shows an increased risk in a specific location, the platform may recommend reassigning that worker to a different region.

In some embodiments, feedback may be provided to individual workers relating their performance to the performance of others. This may be in the form of a rank on a leaderboard, for example.

The platform may further advise on shift changes. In this embodiment, workers who are at increased risk of injury after a certain number of hours of their shift because of fatigue, or other reasons, can be shifted to another task that uses alternate muscles in order to reduce their risk of fatigue induced injuries. In addition, the unloading or loading of a trailer, or other high intensity tasks, can be scheduled to coincide with times of the shift where workers at least fatigued.

Figure 5:
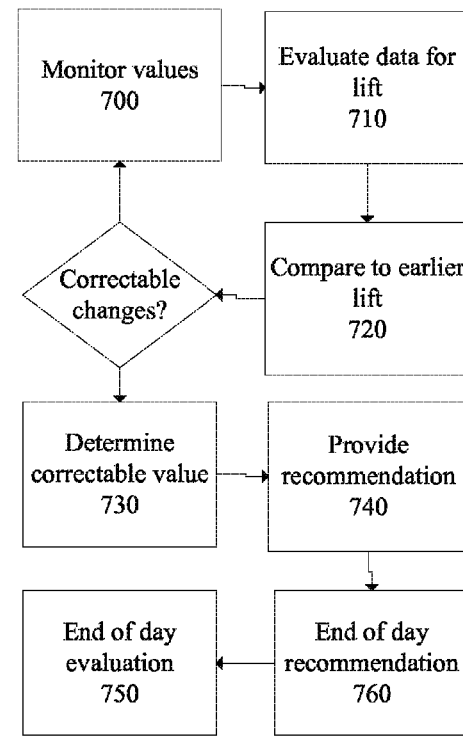
FIG. 5 illustrates an alternate method for generating recommendations.

FIG. 5 illustrates an alternate method for generating recommendations. As shown in the figure, the server monitors (700) the values of the risk metric determined in the method of FIG. 3 across multiple lifts for a specific user. If a specific one of the lifting activities performed by the user demonstrates increased risk as measured by the risk metric, the platform evaluates (710) the data underlying the specific lift being evaluated. The platform then compares (720) each of the underlying metrics to the corresponding metrics determined for earlier lifts performed by the same worker.

If the underlying metrics differ in a specific identifiable way from earlier lifts, the platform determines (730) if the underlying metrics is correctable by the user, and if so, provides a recommendation (740) to address the change. For example, where the platform notes that the horizontal distance between the workers back and wrist has changed, or the user's back angle has shifted, it may recommend correcting the user's posture. The platform may determine that the value has changed by checking each value underlying the metric for each lift against the average value of the corresponding measurement. If there is a significant difference, such as if the value differs by more than a threshold percentage, the platform may recommend a corresponding change.

Further, in some embodiments, if the risk as described by the model is above a threshold, the individual components of the risk models may be analyzed to determine the cause of the underlying risk, and to present recommendations for addressing the high risk level. For example, if the risk metric provides an increased value and the platform determines that the frequency multiplier is abnormally high, recommendations may be provided based on reducing the frequency rates of lifts or having more people perform the job so as to reduce the load on each individual worker.

This recommendation may be provided to a worker as soon as detected by the platform by providing feedback corresponding to the aspect of the worker's posture that should be addressed. For example, where the distance between wrist and back has changed, haptic feedback may be applied to the worker's wrist, while if the back angle has changed, such feedback may be applied to the user's back.

Additional recommendations may be generated by the platform. For example, depending on the values for the variables underlying the risk metric, the platform may recommend bringing a load closer to the worker by removing any barriers or obstacles between the worker and the load, avoiding lifts beginning near the floor, avoiding lifts over shoulder height, reducing the vertical distance between the origin and the destination of a load, reducing a lifting frequency, or allowing for longer recovery periods between lifts. Further, the platform may recommend improving posture by straightening the worker's back and lifting with his legs or turning feet and stepping to move loads rather than having a worker twist his back.

In addition to recommendations, the a platform implementing the method may generate actionable visualizations by summarizing metrics recorded over the course of an evaluation period, or over an extended period of time, by providing charts indicating high risk times of days, weeks, or months, so that specific risks may be identified and addressed. The platform may further identify, for example, a percentage of high risk lifts or total number of high risk lifts performed in a specified period of time.

Such an evaluation may be done in real-time by providing such feedback during a work shift. Alternatively, or in addition, the platform may provide (750) an end of day evaluation. Such an evaluation may, for example, demonstrate worsening posture over the course of the day indicating fatigue. In such a scenario, the platform may provide a recommendation (760) such as a scheduling change or a reorganization of tasks. For example, the platform may recommend lifting heavier objects earlier in a shift.

While the method is described with respect to a risk metric, the method may further be used to monitor productivity across tasks for individual workers. This may be by monitoring, for example, frequency of lifts, or productivity over the course of a shift. For both the methods illustrated in FIGS. 4 and 5, where recommendations are made, the results of those recommendations may be monitored based on the productivity metric as well as the risk metric in order to evaluate whether the recommended change was effective. Accordingly, where a piece of equipment was recommended and implemented in a specific location, the platform may monitor future activity in that location to determine if injury risk has in fact decreased and/or to determine if productivity has in fact increased in that location. This information can be incorporated into future modeling of that particular change.

Metrics relating to productivity of individual workers may be further developed, and productivity based metrics may be utilized to evaluate relationships between fatigue and productivity. Accordingly, the platform may provide estimates of return on investment for individual pieces of equipment that may both reduce injury risk and increase productivity. In some cases, a reduction in injury risk may lower productivity, while a requirement for a worker increasing productivity may increase the risk for that particular worker. The platform described may determine an appropriate balance of increasing a worker's productivity while maintaining the risk metric below a specified threshold.

In some embodiments, fatigue of workers may be evaluated by estimating energy associated with motion of the worker. Fatigue affects risk and is typically incorporated into measurements in the form of lift rate, and in generating an effective weight lifted, as discussed above with respect to step 490. Fatigue may be further evaluated by monitoring average acceleration rates of the wrist and back of the worker over time, including during non-lifting activities, such as inventory checking or manufacturing processes. By detecting reductions in acceleration rates over time, such a method may then identify fatigue and determine potential and kinetic energies expected by a workers body.

The platform described may provide immediate feedback to workers themselves, or it may provide feedback directly to managers, either through on screen notifications at their workstations or through text messages to immediately notify a manager to an increase risk level for an employee. Similarly, the platform may provide rankings for individual workers, or may alert the manager when the workplace as a whole has generated an increased risk profile.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" and like terms encompass all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A computer-based method for identifying risk during physical activities comprising:
   locating a wearable first device at a first location on a wearer;
   location a wearable second device at a second location on the wearer;
   receiving a first signal from the wearable first device generated from dynamic activity of the first device over time;
   receiving a second signal from the wearable second device generated from dynamic activity of the second device over time;
   identifying, from the first signal or the second signal, an initiation time for a physical activity performed by the wearer of the first device and the second device;
   excerpting a first signal segment from the first signal for a time period following the initiation time for the physical activity;
   excerpting a second signal segment from the second signal for the time period following the initiation time for the physical activity;
   determining a conclusion time for the physical activity;
   calculating measurements of the wearer for the time period during the physical activity from the first signal segment and the second signal segment; and calculating a risk metric from a risk model based on the measurements of the wearer for the time period during the physical activity, the risk metric being indicative of high risk physical activity, wherein the initiation time and the conclusion time are each determined based on sensor data from the first device or the second device; and wherein the initiation time for the physical activity is determined prior to the conclusion time for the physical activity.

2. The method of claim 1 further comprising repeating the method to identify a plurality of physical activities over an evaluation period, wherein the excerpted first signal segment and second signal segment are for the time period following the initiation time and prior to the conclusion time for the physical activity.

3. The method of claim 2 further comprising defining a particular activity for each physical activity of the evaluation period.

4. The method of claim 3 further comprising evaluating instances of the risk metric corresponding to a particular activity and generating a recommendation for reducing the value of the risk metric for future instances of the defined physical location or particular activity.

5. The method of claim 4 wherein the recommendation comprises one of:
a recommendation to bring a load closer to the wearer by removing any barriers or obstacles between the wearer and the load;
a recommendation to avoid lifts beginning near the floor;
a recommendation to avoid lifts over shoulder height;
a recommendation to reduce the vertical distance between an origin and a destination of a load;
a recommendation to reduce a lifting frequency;
a recommendation that the wearer modify his posture or biomechanics in a specified way; or
a recommendation to allow for longer recovery periods between lifts.

6. The method of claim 3 wherein at least one physical activity of the evaluation period is defined as a first particular activity and at least one other particular activity of the evaluation period is defined as a second particular activity, the method further comprising calculating a cumulative risk metric indicative of high risk physical activity over time based on the calculated risk metric and the identity of the first and second particular activity and outputting feedback indicative of a high risk when the cumulative risk metric is above a threshold level.

7. The method of claim 2 wherein the measurements extracted are:
a horizontal location of the first device relative to a second device;
a vertical location of the first device relative to a floor;
a rotation angle of the second device;
a frequency of physical activities during the evaluation period; and
a duration of the evaluation period.

8. The method of claim 7 wherein the risk metric is a maximum weight for a package lifted that should not be exceeded.

9. The method of claim 7 further comprising receiving a predetermined average weight of packages to be lifted during the evaluation period, and wherein the risk metric is an estimated risk of injury.

10. The method of claim 2 wherein the measurements extracted are:

an average twisting velocity of the torso of the user;
a maximum moment on the lower back;
a maximum bending angle of the lower back relative to gravity;
a maximum lateral velocity of the torso; and
a frequency of lifting activities among the physical activities during the evaluation period.

11. The method of claim 2 further comprising calculating a productivity metric independent of the risk metric based on a total number of physical activities over the evaluation period and the duration of each physical activity.

12. A system for identifying risk during physical activities comprising:
a first wearable device located at a first location on a wearer;
a second wearable device located at a second location on the wearer;
a computing device having a memory and a processor in communication with the first wearable device and the second wearable device;
wherein the computing device:
receives a first signal from the first wearable device generated from dynamic activity of the first device over time and a second signal from the second wearable device generated from dynamic activity of the second device over time;
identifies, from the first signal and the second signal, an initiation time for a physical activity performed by a wearer of the first device and the second device,
determines a conclusion time for the physical activity,
excerpts a first signal segment from the first signal and a second signal segment from the second signal for a time period following the initiation time for the physical activity,
calculates measurements of the wearer during the physical activity from the first signal segment and the second signal segment, and
calculates a risk metric from a risk model based on the measurements of the wearer for the time period during the physical activity, the risk metric being indicative of high risk physical activity,
wherein the initiation time and the conclusion time are each determined based on sensor data from the first device or the second device, and
wherein the initiation time for the physical activity is determined prior to the conclusion time for the physical activity.

13. A computer-based method for identifying risk during material handling activities comprising:
receiving a first signal from a wearable first device generated from dynamic activity of the first device over time;
receiving a second signal from a wearable second device generated from dynamic activity of the second device over time;
calculating measurements of a wearer of the first device and the second device during a material handling activity from the first signal and the second signal;
calculating a risk metric from a risk model based on the measurements of the wearer for the time period during the material handling activity, the risk metric being indicative of high risk material handling activity;
repeating the method to identify a plurality of material handling motions over an evaluation period;
extracting data indicative of an angular velocity or acceleration of the first sensor during the material handling activity; and determining a weight of an object handled based at least in part on the angular velocity or acceleration data extracted.

14. The method of claim 13 wherein the metric is an acceptable weight limit for an object handled, the method further comprising outputting feedback indicative of a high risk material handling activity if the weight of the object handled is greater than the acceptable weight limit.

15. The method of claim 1 wherein the physical activity is one of lifting, pushing, pulling, carrying, or throwing.

16. The system of claim 12 wherein the physical activity is one of lifting, pushing, pulling, carrying, or throwing.

17. The method of claim 5 further comprising evaluating instances of the risk metric across a group of wearers, and wherein the recommendation is applied to the group of wearers.

18. The method of claim 2 wherein the risk metric is indicative of forces on a segment of the spine, the method further comprising providing feedback where the risk metric is above a defined threshold.

19. The method of claim 2 wherein the risk metric is indicative of a biomechanical posture during the physical activity, the method further comprising providing feedback where a value for the risk metric derived from the posture detected deviates from a predetermined ideal value for the risk metric.

20. The method of claim 2 wherein the risk metric is indicative of dynamic variables representing position, velocity, and acceleration of the wearable second device, the method further comprising providing feedback when that value is above a defined threshold.

21. The method of claim 14 wherein the material handling activity is one of lifting, pushing, pulling, carrying, or throwing.

22. The method of claim 2 wherein the second location on the wearer is a torso or waist of a user and the measurements extracted are kinematic measurements of the wearer's torso, including position, velocity, or acceleration of the torso in one or more of the cardinal planes.

23. The method of claim 1, wherein the first location on the wearer is an arm and the initiation time is identified by identifying movement of the first device above a wearer's shoulder.

24. The method of claim 11, further comprising generating recommendations for increasing the value of the productivity metric while reducing the value of the risk metric.

25. The method of claim 1, further comprising calculating the risk metric prior to the conclusion time and outputting feedback indicative of a high risk prior to the conclusion time.

* * * * *